(12) United States Patent
Croizat et al.

(10) Patent No.: US 9,211,364 B2
(45) Date of Patent: Dec. 15, 2015

(54) CONNECTION DEVICE FOR MERGING AT LEAST TWO LINE SECTIONS IN A VACUUM WOUND TREATMENT SYSTEM

(75) Inventors: Pierre Croizat, Herbrechtingen (DE); Axel Eckstein, Heidenheim (DE); Jürgen Hofstetter, Heidenheim (DE)

(73) Assignee: PAUL HARTMANN AG, Heidenheim (DE)

( * ) Notice: Subject to any disclaimer, the term of this patent is extended or adjusted under 35 U.S.C. 154(b) by 322 days.

(21) Appl. No.: 13/816,664

(22) PCT Filed: Jul. 15, 2011

(86) PCT No.: PCT/EP2011/062116
§ 371 (c)(1), (2), (4) Date: Feb. 12, 2013

(87) PCT Pub. No.: WO2012/019865
PCT Pub. Date: Feb. 16, 2012

(65) Prior Publication Data
US 2013/0144234 A1 Jun. 6, 2013

(30) Foreign Application Priority Data
Aug. 13, 2010 (DE) .......................... 10 2010 034 292

(51) Int. Cl.
*A61M 1/00* (2006.01)
*A61M 39/10* (2006.01)
*A61M 3/00* (2006.01)
(Continued)

(52) U.S. Cl.
CPC ........... *A61M 1/0023* (2013.01); *A61M 1/0086* (2014.02); *A61M 39/10* (2013.01); *A61M 39/105* (2013.01); *A61M 1/0058* (2013.01);
(Continued)

(58) Field of Classification Search
CPC . A61M 39/10; A61M 39/105; A61M 1/0089; A61M 1/0086; A61M 1/0058
USPC ................. 604/319, 305, 43; 137/614.03
See application file for complete search history.

(56) References Cited

U.S. PATENT DOCUMENTS 5,059,170 A * 10/1991 Cameron .................. 604/43
5,286,067 A    2/1994 Choksi
(Continued)

FOREIGN PATENT DOCUMENTS

DE    31 27 249    6/1982
DE    G 85 35 050.8    3/1986
(Continued)

*Primary Examiner* — Tatyana Zalukaeva
*Assistant Examiner* — Andrew J Mensh
(74) *Attorney, Agent, or Firm* — Henry M. Feiereisen LLC

(57) ABSTRACT

The invention relates to a connection device for merging at least two line sections in a vacuum-based wound treatment system, wherein the two line sections are arranged on the wound side in relation to the connection device, and wherein the connection device, on the side thereof facing away from the wound, can be connected to a third, multi-lumen line section leading to a vacuum-generating device; the connection device is designed, according to the invention, such that the at least two line sections have a multi-lumen configuration and these line sections each have a multi-lumen attachment device that can be brought into flow communication with the connection device, and such that separate lumens of the two line sections on the wound side also remain separate from each other inside the connection device and inside the third line section.

7 Claims, 2 Drawing Sheets

(51) Int. Cl.
 *A61F 13/00* (2006.01)
 *E03B 1/00* (2006.01)
 *A61M 39/00* (2006.01)

(52) U.S. Cl.
 CPC ............ *A61M1/0084* (2013.01); *A61M 1/0088* (2013.01); *A61M 2039/0009* (2013.01)

(56) References Cited

U.S. PATENT DOCUMENTS

| | | | |
|---|---|---|---|
| 5,527,293 A * | 6/1996 | Zamierowski | ................ 604/176 |
| 5,662,616 A * | 9/1997 | Bousquet | ................ 604/175 |
| 6,367,510 B1 | 4/2002 | Carlson | |
| 6,969,381 B2 * | 11/2005 | Voorhees | ................ 604/534 |
| 7,658,205 B1 | 2/2010 | Edelman et al. | |
| 2005/0046184 A1 | 3/2005 | Chang et al. | |
| 2005/0256461 A1 * | 11/2005 | DiFiore et al. | ................ 604/247 |
| 2008/0011368 A1 | 1/2008 | Singh et al. | |
| 2009/0131892 A1 | 5/2009 | Karpowicz et al. | |
| 2013/0131616 A1 * | 5/2013 | Locke | ................ 604/321 |

FOREIGN PATENT DOCUMENTS

| | | |
|---|---|---|
| DE | G 88 15 869.1 | 3/1989 |
| DE | 698 18 190 | 6/2004 |

\* cited by examiner

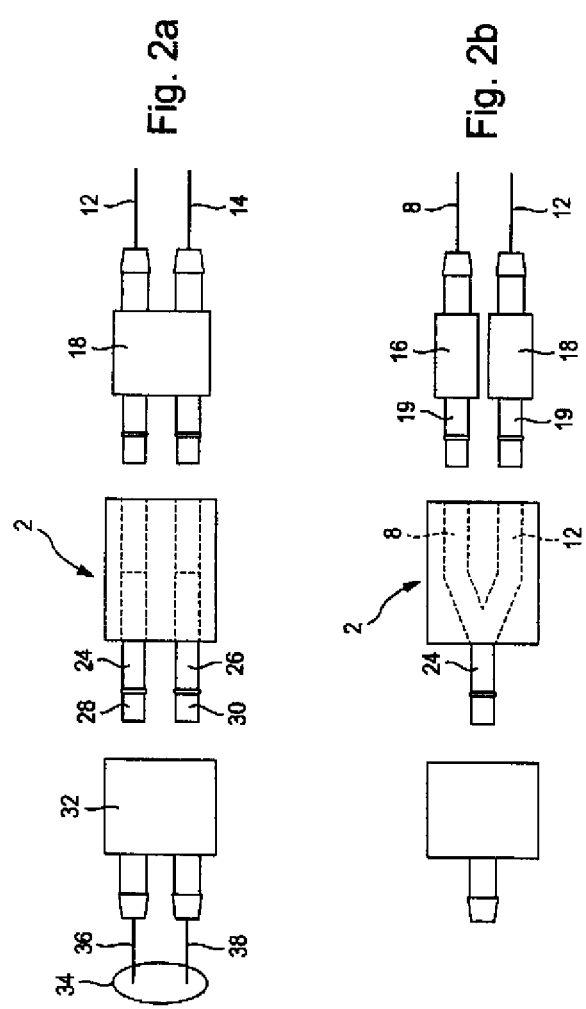

CONNECTION DEVICE FOR MERGING AT LEAST TWO LINE SECTIONS IN A VACUUM WOUND TREATMENT SYSTEM

CROSS-REFERENCES TO RELATED APPLICATIONS

This application is the U.S. National Stage of International Application No. PCT/EP2011/062116, filed Jul. 15, 2011, which designated the United States and has been published as International Publication No. WO 2012/019865 A1 and which claims the priority of German Patent Application, Serial No. 10 2010 034 292.0 filed Aug. 13, 2010, pursuant to 35 U.S.C. 119(a)-(d).

BACKGROUND OF THE INVENTION

The invention relates to a connection device for merging at least two line sections in a vacuum wound treatment system, wherein the two line sections are arranged on the wound side in relation to the connection device and lead to different wound connections for one wound or two wound connections for different wounds of the same patient, wherein the connection device is connectable on its side which faces away from the wound with a third multi-lumen line section which leads to a vacuum generating device.

The applicant assumes that such typically Y-shaped connection devices for merging two line sections into a third line section are known.

Based on the foregoing, the inventing is based on the object to propose a connection device which allows establishing a multi-lumen fluid communication to at least two wound connections, wherein the term "fluid" is to be understood in the broadest sense and is intended to include the transmission of liquids or gases or the generation of a vacuum.

SUMMARY OF THE INVENTION

According to the invention, this object is solved by a connection device of the aforementioned type, which is characterized in that the at least two line sections are configured multi-lumen, and these line sections each have a respective multi-lumen attachment device which can be brought into flow communication with the connection device and in that lumens of the two wound-side line sections which are separated from one another also remain separated from one another within the connection device and within the third line section.

Thus, it is possible to couple two line sections which are configured multi-lumen and which derive from a respective wound connection and each have an attachment device, for example a pluggable and in particular latchingly engageable attachment device, with the one connection device for example by plug-in connection, threaded connection or the like. In the interior of the connection device, mutually corresponding lumens of the line sections are then merged and brought into flow communication with one of the multiple lumens of the third line section which leads to the vacuum generating device. This connection can advantageously also be established for example by means of a pluggable and in particular latchingly engageable attachment device on the third line section.

According to the invention, it is ensured that lumens of the two wound-side line sections which are separate from one another also remain separated in the further course. This is what enables the use of the at least two lumens of a respective line section for different purposes in the first place. For example, a lumen may be used for applying negative pressure on the wound and another lumen as rinsing channel for supplying a gaseous of liquid rinsing medium in the direction toward the wound and/or toward an exit region of the first, mentioned lumen near the wound.

The mentioned connection device may generally be formed from multiple parts which are separated from one another, in particular from multiple Y-type connection elements which interact with the respective attachment devices of the line sections. In a refinement of the invention, it is proposed however, that the connection device is formed by a one-piece connection part, which can in particular and preferably be an injection molded part. The one-piece connection part mentioned above does not imply that no additional sealing means such as for example O-rings or auxiliary sealing means or the like may be provided. A one-piece connection part according to the present invention means rather that the connection piece is formed from a single housing part.

According to a preferred embodiment of the invention, two wound-side lumens are merged in the interior of the connection device into one lumen which faces away from the wound. It would also be conceivable however, that the connection device is configured for more than two wound-side line sections which themselves have two or more lumens.

In a further embodiment of the invention, it is proposed that the respective merging of the at least two wound-side lumens into the one lumen which faces away from the wound is arranged in one plane. This allows for a relatively simple construction of the connection device.

Further, it is advantageous when the multi-lumen line sections and the connection device and the respective attachment devices have a side-by-side arrangement of the lumens on the line sections. This also simplifies the configuration of the attachment devices on the respective line sections and the connection device according to the invention because this results in a less complex construction and production of the coupling regions which seal towards the outside.

Further, it is useful when the connection device has on one side, in particular wound-side, female receptacles for the respective attachment devices and on the other side, in particular on the side facing away from the wound, male connections for the respective attachment devices. However, the inverse is also conceivable.

As mentioned in the beginning, it is advantageous when one of the lumens of the separated lumens of the line sections and the connection device is configured for applying negative pressure to a wound and another lumen is configured as rinsing channel for supplying a gaseous or liquid rinsing medium in the direction toward the wound and/or toward an exit region near the wound of the first mentioned lumen.

In this case, it is advantageous when a lumen of the third line section which faces away from the wound, is in flow communication with a rinsing connection which can be opened and closed in a controlled manner, in order to conduct a gaseous or liquid rinsing medium in the direction toward the wound and/or toward a exit region near the wound of a lumen of the line sections which faces toward the wound.

The invention further relates to the use of the connection device according to the invention, in which a negative pressure is applied on a lumen which faces away from the wound and a gaseous or liquid rinsing medium is supplied in a controlled manner and intermittently, i.e. not continuously, on another lumen which faces away from the wound in order to remove or prevent a clogging of the second mentioned lumen.

A further subject matter of the present invention is a combination of a basic body, having a wound proximate side, a wound distal side and internal lumens and at least two multi-lumen line sections, wherein the two line sections are arranged on the side of the wound in relation to the connection device and each have an attachment device for coupling with the connection device, and a third multi-lumen line section provided on the side of the connection device which faces away from the wound, of which at least one lumen is connectable with a vacuum generating device and at least one lumen is connectable with a controllable connection for supplying a fluid rinsing medium.

BRIEF DESCRIPTION OF THE DRAWING

Further features, details and advantages of the invention result from the included patent claims and the drawing and the following description of the preferred embodiments of the connection device. In the drawing, it is shown in:

FIGS. 2a+2b show a plan view and a side view of the components according to FIG. 1.

DETAILED DESCRIPTION OF PREFERRED EMBODIMENTS

Figure 1:
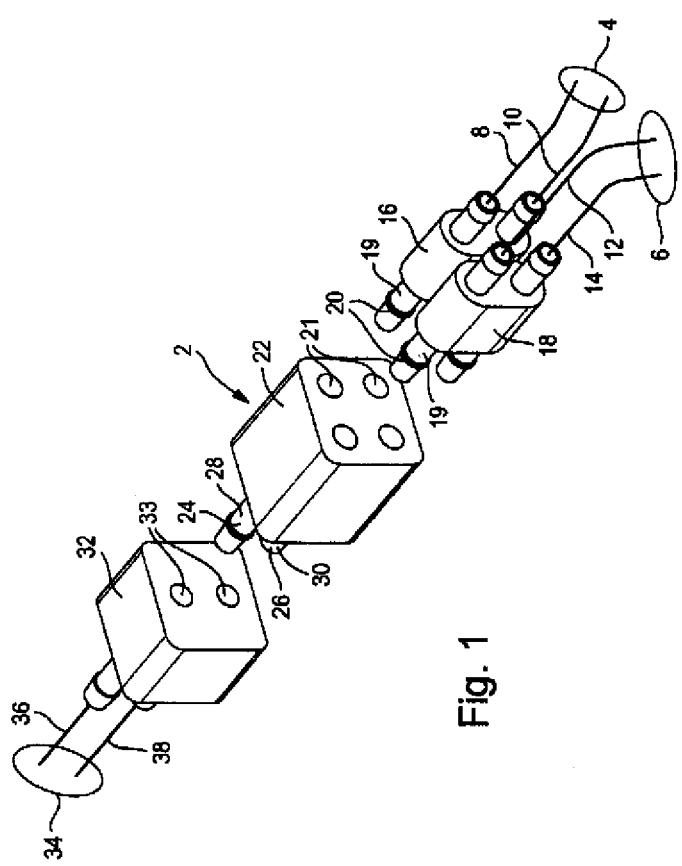
FIG. 1 a perspective view of the connection device according to the invention with wound-side attachment devices and attachment devices facing away from the wound with multi-lumen line sections which are only shown schematically.

The Figures show a connection device 2 according to the invention for merging at least two two-lumen line sections 4, 6 which are only shown schematically and lead to one or multiple wounds i.e., to essentially vacuum tight wound covers or wound connections (not shown). The line sections 4, 6 each have two lumens 8, 10 or 12, 14. The line sections 4, 6 or their lumens 8, 10 and 12, 14 are provided with attachment devices 16, 18 for example in the manner of plug-in adapters so as to be sealed towards the outside. These attachment devices 16, 18 which in the exemplary case are provided with male connection plugs 19 can themselves be brought into flow communication with the connection device 2 so as to be sealed pressure tight toward the outside. For this, the connection device 2 in the exemplary shown case is configured with female receptacles 21 for the male connection plug 19 of the attachment devices 16, 18. For the tight sealing, the attachment devices 16, 18 have sealing means in the form of O-rings 20 on their connection plugs 19.

In the exemplary shown case, the connection device 2 includes a preferably one-piece basic body 22, which in the exemplary case may advantageously be an injection molding part.

In a manner which is to be described in more detail below, the lumens 8, 12 and 10, 14 of the line sections 4, 6 are merged in the interior of the connection device 2 into a respective lumen 24, 26 which faces away from the wound. As can be seen in FIGS. 2a and 2b, this is implemented in that in the interior of the connection device 2 the lumens 8, 12 and 10, 14 of the line sections 4 or 6 are each merged in one plane, i.e., two lumens into one lumen. On its side which faces away from the wound, the connection device 2 has two one-lumen outlets, which in the exemplary shown case are configured as male plug parts 28, 30 and interact with an attachment device 32 which has female receptacles 33 and faces away from the wound. The attachment device 32 is itself in flow communication with a two-lumen line section 34 with lumens 36, 38 and leads to a not shown vacuum generating device.

Particularly advantageously, the lumens 36, 38 of the line section 34 which faces away from the wound do not both communicate with a vacuum generating device, but rather one of the lumens 36, 38 is advantageously configured as rinsing channel for supplying a fluid, i.e. gaseous or liquid rinsing medium which if needed and/or in dependence on defined requirements can be released in a controlled manner in the direction towards the wound. In this way, based on a single vacuum generating device and a rinsing device (both not shown) a vacuum can be applied simultaneously via two line sections 4, 6 which are separated from one another to different wound connections of the same wound or wound connections of multiple wounds of the same patient, and on the other hand a possibility of rinsing to each wound connection is provided.

What is claimed is:

1. A connection device for merging at least two line sections in a vacuum wound treatment system, comprising:
a basic body, having a wound proximate side, a wound distal side and internal lumens;
at least two line sections arranged on the wound proximate side, each said at least two line sections having multiple separated lumens and a first multi-lumen attachment device; and
another line section arranged on the wound distal side and having multiple separated lumens,
wherein the basic body is constructed for connection of the internal lumens to the multiple lumens of the at least two line sections on the wound proximate side via the attachment device and for connection of the internal lumens to the multiple separated lumens of the other line section so that the separated lumens of each of the at least two line sections remain separated within the basic body and within the other line section, wherein the internal lumens of the basic body are configured for merging the multiple lumens of one of the at least two line sections with the multiple lumens of the other one of the at least two line sections in one to one correspondence into one wound distal lumen.

2. The connection device of claim 1, wherein the other line section has a second multi-lumen attachment device for connection of the multiple separated lumens of the other line section to the internal lumens of the internal lumens of the basic body.

3. The connection device of claim 1, wherein the basic body is configured one-piece.

4. The connection device of claim 1, wherein the basic body is constructed as injection molding part.

5. The connection device of claim 1, wherein the multiple lumens of one of the at least two line sections and the multiple lumens of the other one of the at least two line sections are merged into the one wound distal lumen in respective single planes.

6. The connection device of claim 1, wherein the lumens of the at least two line sections, the lumens of the other line sections, the lumens of the first and second multi-lumen attachment devices, and the internal lumens of the basic body are arranged side-to-side.

7. The connection device of claim 1, wherein one of the lumens of the at least two line sections, the other line section and the basic body is configured for applying a negative pressure to a wound and another one of the lumens of the at least two line sections the other line section and the basic body is configured as a rinsing channel for supplying a gaseous or liquid rinsing medium in a direction towards the wound and/or toward an exit region of the one of lumens.

* * * * *